United States Patent
Moon (10) Patent No.: US 10,092,751 B2
(45) Date of Patent: Oct. 9, 2018

(54) PORTABLE BODY-CONTACT THERAPEUTIC DEVICE

(71) Applicant: Myeong Keon Moon, Seoul (KR)

(72) Inventor: Myeong Keon Moon, Seoul (KR)

(*) Notice: Subject to any disclaimer, the term of this patent is extended or adjusted under 35 U.S.C. 154(b) by 331 days.

(21) Appl. No.: 15/104,606

(22) PCT Filed: Dec. 2, 2014

(86) PCT No.: PCT/KR2014/011682
§ 371 (c)(1),
(2) Date: Jun. 15, 2016

(87) PCT Pub. No.: WO2015/093753
PCT Pub. Date: Jun. 25, 2015

(65) Prior Publication Data
US 2018/0161575 A1    Jun. 14, 2018

(30) Foreign Application Priority Data

Dec. 16, 2013  (KR) .................. 10-2013-0156521

(51) Int. Cl.
*A61N 1/36* (2006.01)
*A61N 1/32* (2006.01)
(Continued)

(52) U.S. Cl.
CPC ............ *A61N 1/36007* (2013.01); *A61F 7/12* (2013.01); *A61H 19/34* (2013.01); *A61H 19/44* (2013.01); *A61H 23/02* (2013.01); *A61N 1/04* (2013.01); *A61N 1/0484* (2013.01); *A61N 1/32* (2013.01); *A61N 1/321* (2013.01); *A61N 1/36017* (2013.01); *A61F 2007/005* (2013.01); *A61F 2007/0022* (2013.01); *A61F 2007/0086* (2013.01); *A61F 2007/0094* (2013.01); *A61H 2201/0157* (2013.01);
(Continued)

(58) Field of Classification Search
None
See application file for complete search history.

(56) References Cited

FOREIGN PATENT DOCUMENTS

| JP | 2000-51172 | 2/2000 |
|----|------------|--------|
| JP | 2000-512516 | 9/2000 |

(Continued)

*Primary Examiner* — Brian T Gedeon
(74) *Attorney, Agent, or Firm* — Lex IP Meister, PLLC (57) ABSTRACT

The present invention relates to a portable body-contact therapeutic device comprising a main body having a first main body member and a second main body member combined in a clip form such that pants, panties or a belt are worn by being inserted between the opposing surfaces from one side, characterized in that in a state that the pants, the panties or the belt are worn by being inserted in the main body, the outer surface of the first main body member is formed toward the body outside and the outer surface of the second main body member is formed so as to contact the body skin, wherein a current output circuit for outputting a current is included on the inside of the main body, and a main body electrode pad to which the current outputted from the current output circuit is applied is formed in the outer surface of the second main body member. According to the present invention, it is possible to provide a portable body-contact therapeutic device which can easily be worn so as to directly contact the body, and which can maximize the therapy effect for each of various women's diseases.

8 Claims, 10 Drawing Sheets

(51) Int. Cl.
  *A61N 1/04* (2006.01)
  *A61H 23/02* (2006.01)
  *A61F 7/12* (2006.01)
  *A61H 19/00* (2006.01)
  *A61F 7/00* (2006.01)

(52) U.S. Cl.
  CPC .. *A61H 2201/0207* (2013.01); *A61H 2201/10* (2013.01); *A61H 2201/165* (2013.01); *A61H 2201/5035* (2013.01); *A61H 2201/5043* (2013.01); *A61H 2201/5082* (2013.01)

(56) References Cited

FOREIGN PATENT DOCUMENTS

| | | |
|---|---|---|
| KR | 20-0212031 | 2/2001 |
| KR | 20-0307924 | 3/2003 |
| KR | 10-0615073 | 8/2006 |
| KR | 10-1039636 | 6/2011 |
| KR | 20-0454796 | 7/2011 |
| KR | 10-2011-0118602 | 10/2011 |

PORTABLE BODY-CONTACT THERAPEUTIC DEVICE

BACKGROUND

1. Technical Field

The present invention relates to a therapeutic device and, more particularly, to a portable body contact therapeutic device which can be conveniently worn on the body so that it directly touches the body and can maximize therapy effects for various woman diseases.

2. Description of the Related Art

The present invention relates to a therapeutic device for treating body diseases, particularly, feminine diseases using an electric current of a specific frequency.

In today's society, woman's vaginal diseases tend to suddenly increase.

Particularly, 30% or more of the population suffers from urinary incontinence diseases. Various modern diseases, such as a uterus mass, a feeling of cold, cramps, and anorgasmia, tend to greatly increase.

Furthermore, in the case of the feminine diseases, a patient needs to directly visit obstetrics and gynecology and to receive intensive treatment, but is reluctant to receive the treatment for a reason of personal privacy, etc.

Today, a feminine disease treatment device personally used by women can treat only a single disease, and is inconvenient to carry and use due to its bulky size.

Particularly, a feminine disease treatment device which is rarely seen to an eye and can be conveniently worn on the body is rarely provided.

A technology, that is, the background of the present invention, has been disclosed in Korean Patent No. 1006068. The Korean Patent No. 1006068 does not suggest a solution to the aforementioned problems.

SUMMARY

An object of the present invention which has been derived to solve the aforementioned problems is to provide a portable body contact therapeutic device, which has been reduced in size so that it can be conveniently worn on pants, a skirt or a belt, which enables therapy modes for various feminine diseases to be selected, which can perform treatments for a low frequency current and a middle frequency current and treatments according to heat and/or vibration at the same time so that electrical treatments for feminine diseases are made possible, which can properly perform treatments for the lower portion of the abdomen or/and the inside of vagina, thereby being capable of conveniently worn on the body so that it directly touches on the body and maximizing therapy effects for various woman diseases.

In accordance with an aspect of the present invention for achieving the above object, the present invention provides a portable body contact therapeutic device, including a main body which has a first main body member and a second main body member coupled together in a clip form so that pants, underpants or a belt is worn in such a way as to be inserted between the facing surfaces of the first and the second main body members from one side of the main body. The outside surface of the first main body member is formed to be directed toward the outside of a body and the outside surface of the second main body member is formed to touch the skin of the body in a state in which the pants, underpants or belt has been inserted and worn on the main body. The main body includes a current output circuit which outputs an electric current. A main body electrode pad through which the electric current output by the current output circuit flows is formed on the outside surface of the second main body member.

In this case, the current output circuit includes a low frequency current output circuit which outputs a predetermined low frequency current and a middle frequency current output circuit which outputs a predetermined middle frequency current. The main body electrode pad includes a low frequency electrode plate and a middle frequency electrode plate through which the low frequency current output by the low frequency current output circuit and the middle frequency current output by the middle frequency current output circuit flow, respectively.

Furthermore, the main body further includes a mode selection unit which has two or more therapy modes including a urinary incontinence therapy mode and a cramps therapy mode and in which one of the therapy modes is selected and a micro controller unit (MCU) in which a proper low frequency current value and a proper middle frequency current value are previously set based on a therapy mode selected in the mode selection unit and which controls the operations of the low frequency current output circuit and the middle frequency current output circuit so that a predetermined proper low frequency current value and proper middle frequency current value according to the therapy mode selected in the mode selection unit are output.

Furthermore, the mode selection unit further includes a user age mode selection unit which receives and selects information about ages of two or more users. The MCU is previously programmed so that the low frequency current output circuit and the middle frequency current output circuit output a low frequency current and a middle frequency current suitable for selected age information and a selected therapy mode, respectively, based on the age mode and the therapy mode selected in the mode selection unit.

Furthermore, the main body includes a probe connection terminal which is connected to the current output circuit so that the electric current output by the current output circuit is externally transferred and which is connected to the main body to enable the transmission and reception of external data. A probe electrode pad is connected to the probe connection terminal by an electric wire and formed in a form inserted into a woman's vagina. The probe electrode pad through which the electric current transferred through the electric wire from the probe connection terminal flows is formed on an external surface.

Furthermore, the probe includes a temperature sensor which measures a temperature of a surface of the probe, a heating unit which generates heat, and a vibration unit which generates vibration. The main body further includes a heat generation output circuit which outputs a heat generation signal so that the heating unit generates heat of a specific temperature and which is connected to the probe connection terminal so that the output heat generation signal is transmitted to the heating unit of the probe. The MCU controls an operation of the heat generation output circuit so that the heat generation output circuit outputs the heat generation signal which enables a temperature sensed by the temperature sensor to be maintained at a predetermined proper temperature.

Furthermore, when the cramps therapy mode is selected in the mode selection unit, the MCU controls the operation of the current output circuit so that an electric current does not flow toward the probe connection terminal. When the urinary incontinence therapy mode is selected in the mode selection unit, the MCU controls the operation of the current output circuit so that only one predetermined current of the low frequency current output by the low frequency current output circuit and the middle frequency current output by the middle frequency current output circuit flows toward the probe connection terminal.

Furthermore, the probe includes a vibration unit which generates vibration. The mode selection unit includes a vibration mode selection unit in which a vibration on or off mode and one of two or more vibration intensity modes classified according to vibration intensity may be selected. The main body further includes a vibration generation output circuit which outputs a vibration generation signal so that the vibration unit generates specific vibration and which is connected to the probe connection terminal so that the output vibration generation signal is transmitted to the vibration unit of the probe. The MCU controls the operation of the vibration generation output circuit so that vibration selected in the vibration mode selection unit is generated from the vibration unit.

Furthermore, conductive adhesive pads are coupled to the main body electrode pad and the probe electrode pad, respectively.

DESCRIPTION OF REFERENCE NUMERALS

| 100: main body | 110: first main body member |
|---|---|
| 111: mode selection unit | 112: display unit |
| 120: second main body member | 130: power source unit |
| 140: MCU | 150: current output circuit |
| 151: low frequency current output circuit | |
| 152: middle frequency. current output circuit | |
| 160: main body electrode pad | |
| 170: heat generation output circuit | |
| 180: vibration generation output circuit | |
| 190: probe connection terminal | |
| 200: probe | 210: probe electrode pad |
| 220: temperature sensor | 230: heating unit |
| 240: vibration unit | |

DETAILED DESCRIPTION

The merits and characteristics of the present invention and a method for achieving the merits and characteristics thereof will become more apparent from the following embodiments taken in conjunction with the accompanying drawings.

However, the present invention is not limited to the disclosed embodiments, but may be implemented in various ways. The embodiments are provided to complete the disclosure of the present invention and to enable those skilled in the art to understand the scope of the present invention. The present invention is defined by the claims. The same reference numbers will be used to refer to the same or similar elements throughout the drawings.

Hereinafter, the present invention is described with reference to the drawings for illustrating a portable body contact therapeutic device in connection with the embodiments of the present invention.

Figure 1:
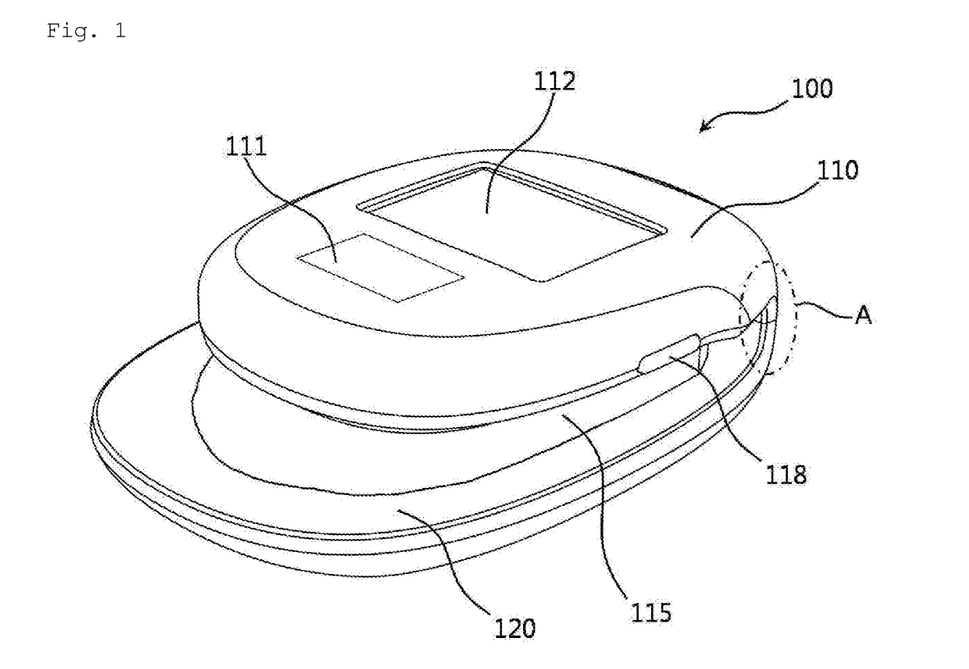
FIG. 1 is a perspective view of a portable body contact therapeutic device according to the present invention.
Figure 2:
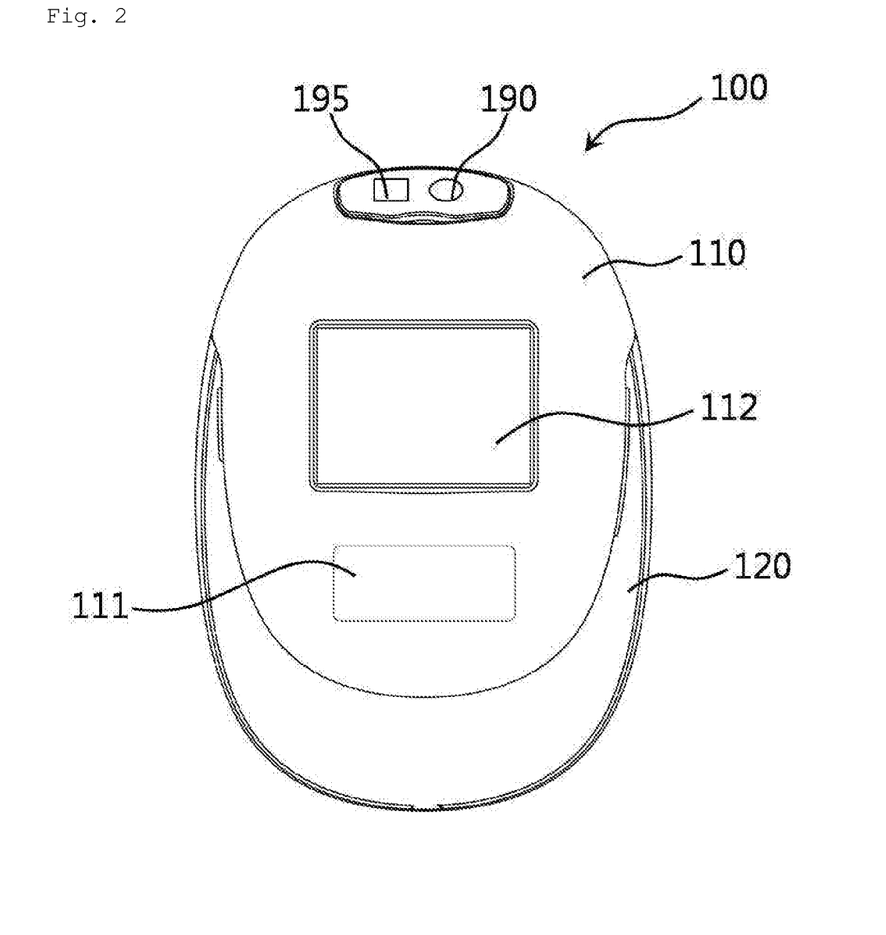
FIG. 2 is a front view of the portable body contact therapeutic device according to the present invention.
Figure 3:
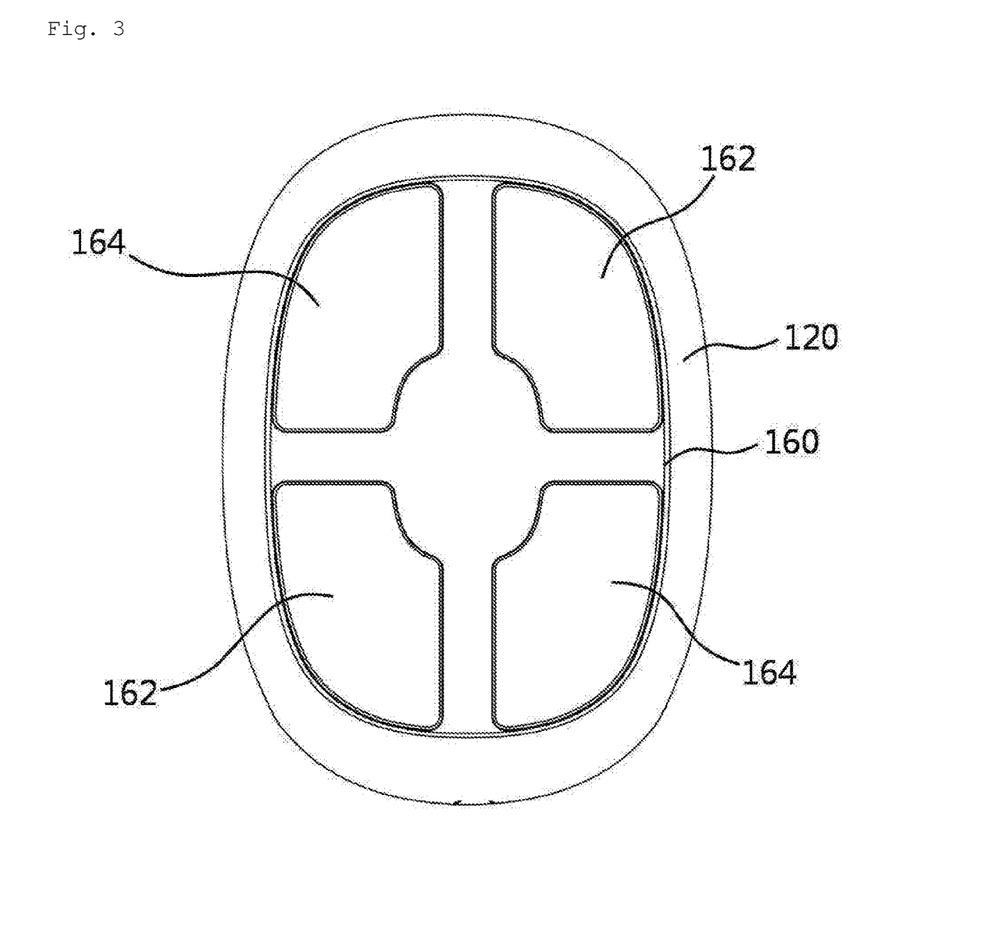
FIG. 3 is a rear view of the portable body contact therapeutic device according to the present invention.
Figure 4:
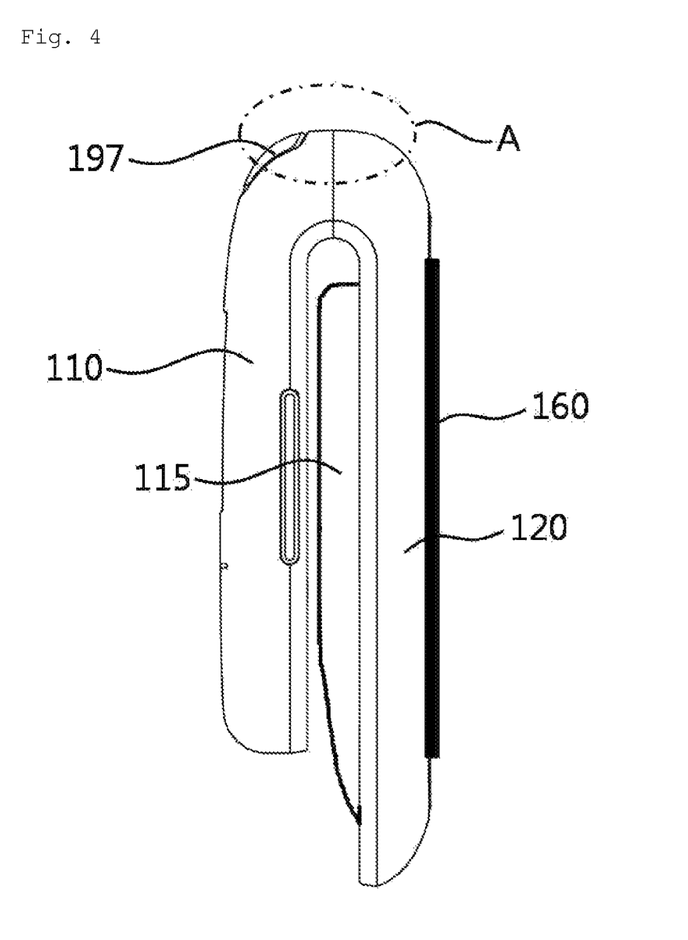
FIG. 4 is a right side view of the portable body contact therapeutic device according to the present invention.
Figure 5:
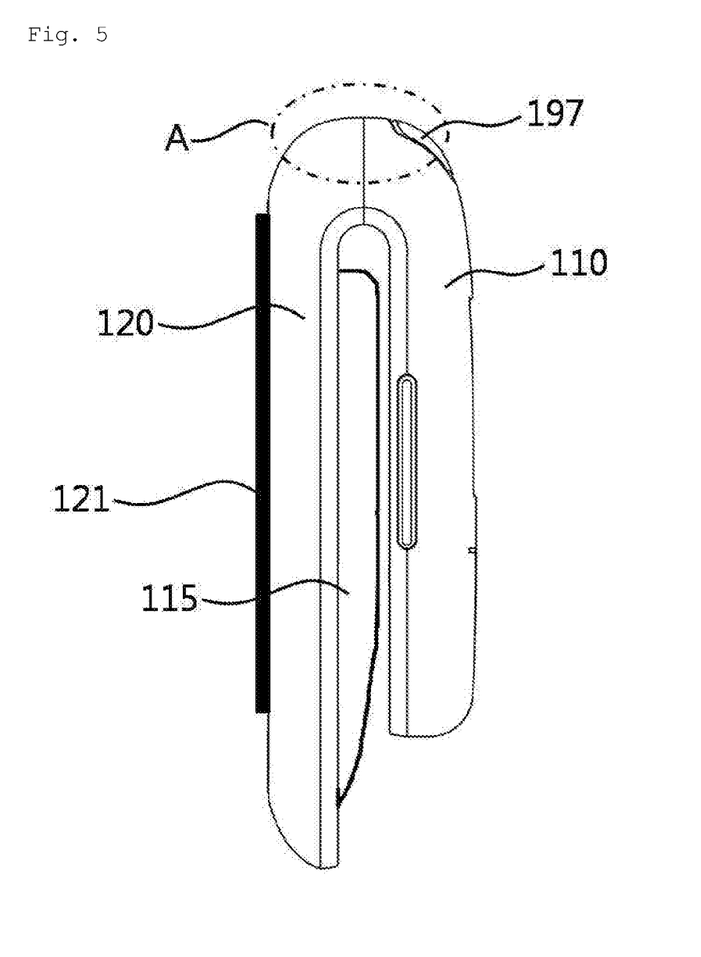
FIG. 5 is a left side view of the portable body contact therapeutic device according to the present invention.

FIG. 1 is a perspective view of a portable body contact therapeutic device according to the present invention, FIG. 2 is a front view thereof, FIG. 3 is a rear view thereof, FIG. 4 is a right side view thereof, and FIG. 5 is a left side view thereof.

Figure 6:
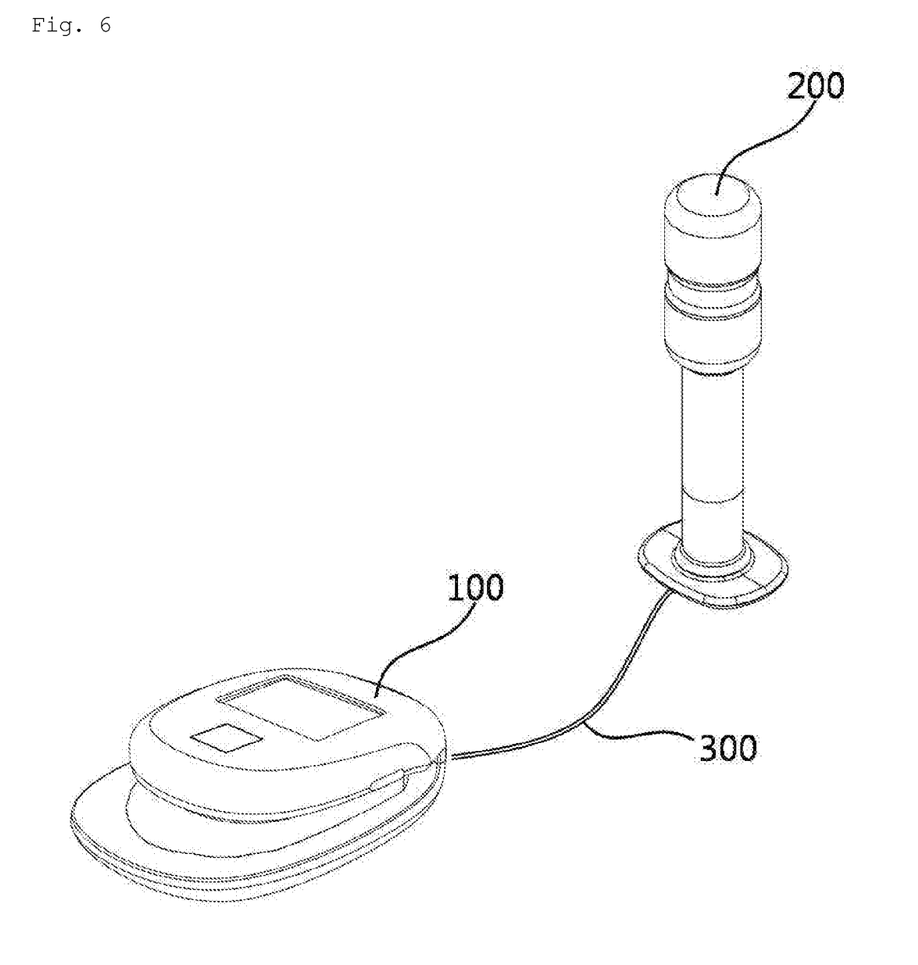
FIG. 6 shows a general configuration in which a probe and a main body have been coupled.
Figure 7:
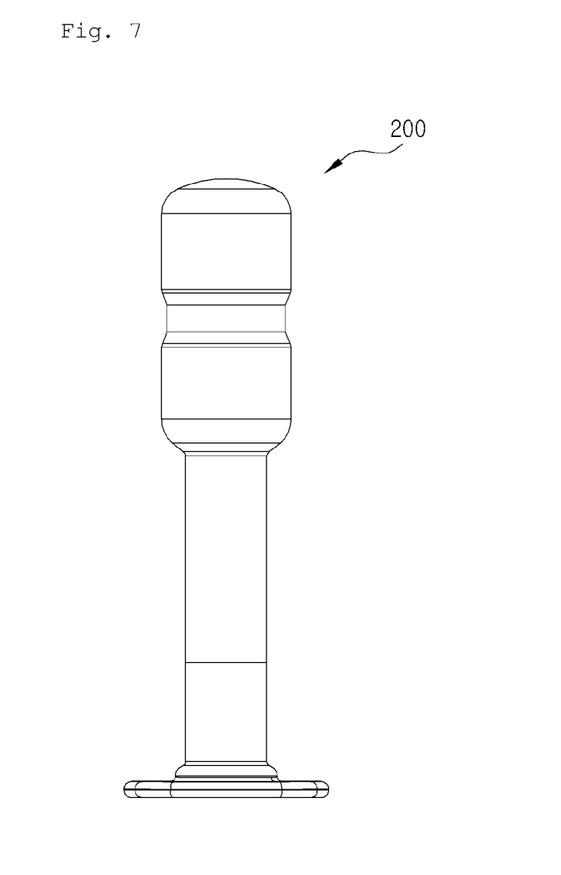
FIG. 7 is a front view of the probe.
Figure 8:
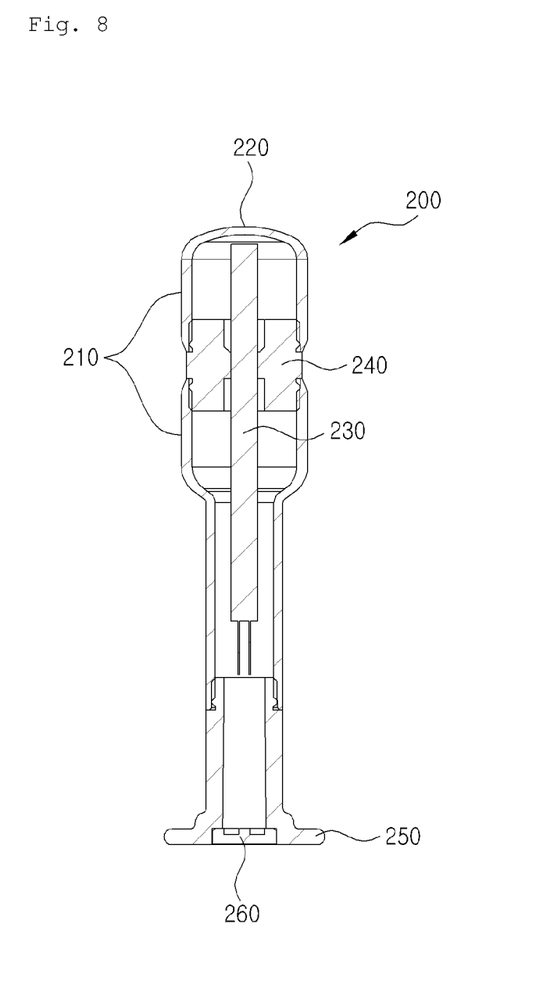
FIG. 8 is a cross-sectional view showing the internal configuration of the probe.

FIG. 6 shows a general configuration in which a probe and a main body have been coupled, FIG. 7 is a front view of the probe, and FIG. 8 is a cross-sectional view showing the internal configuration of the probe.

Figure 9:
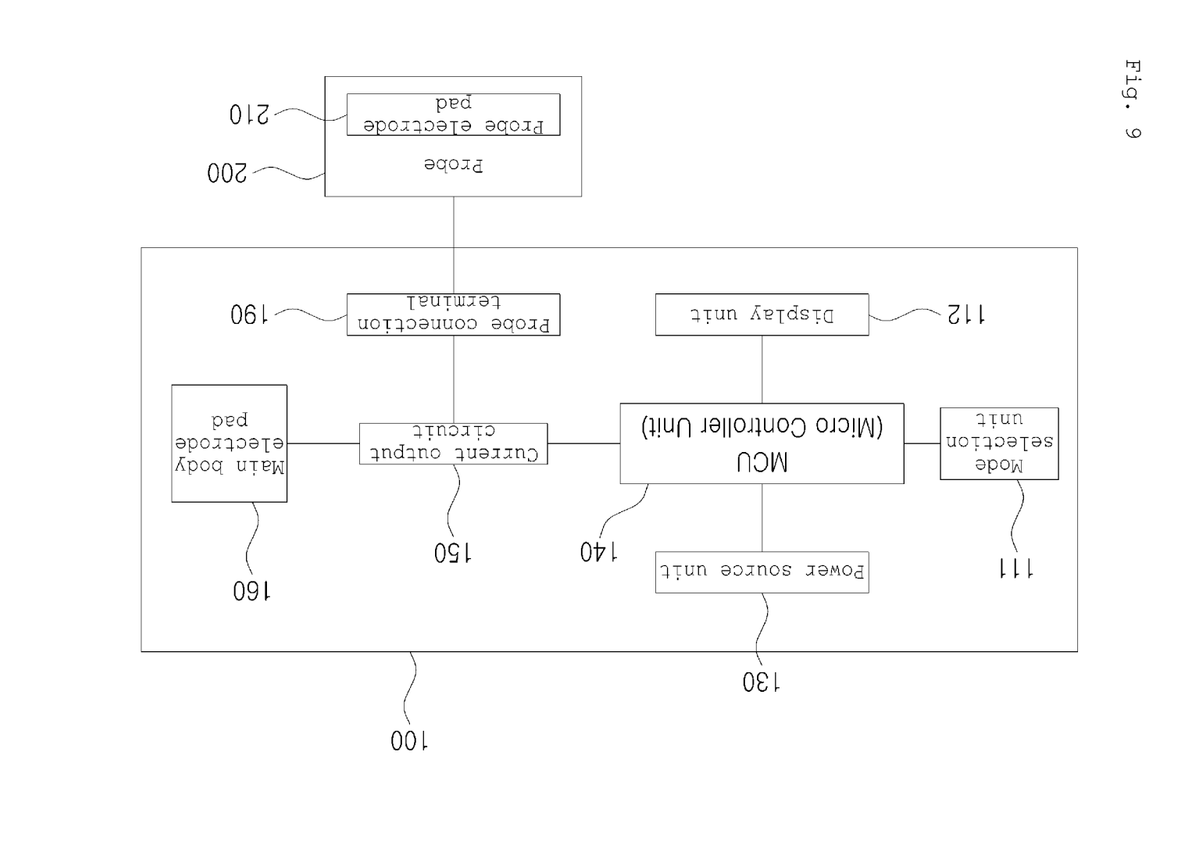
FIGS. 9 and 10 are block diagrams for illustrating the internal configuration of the portable body contact therapeutic device according to the present invention.
Figure 10:
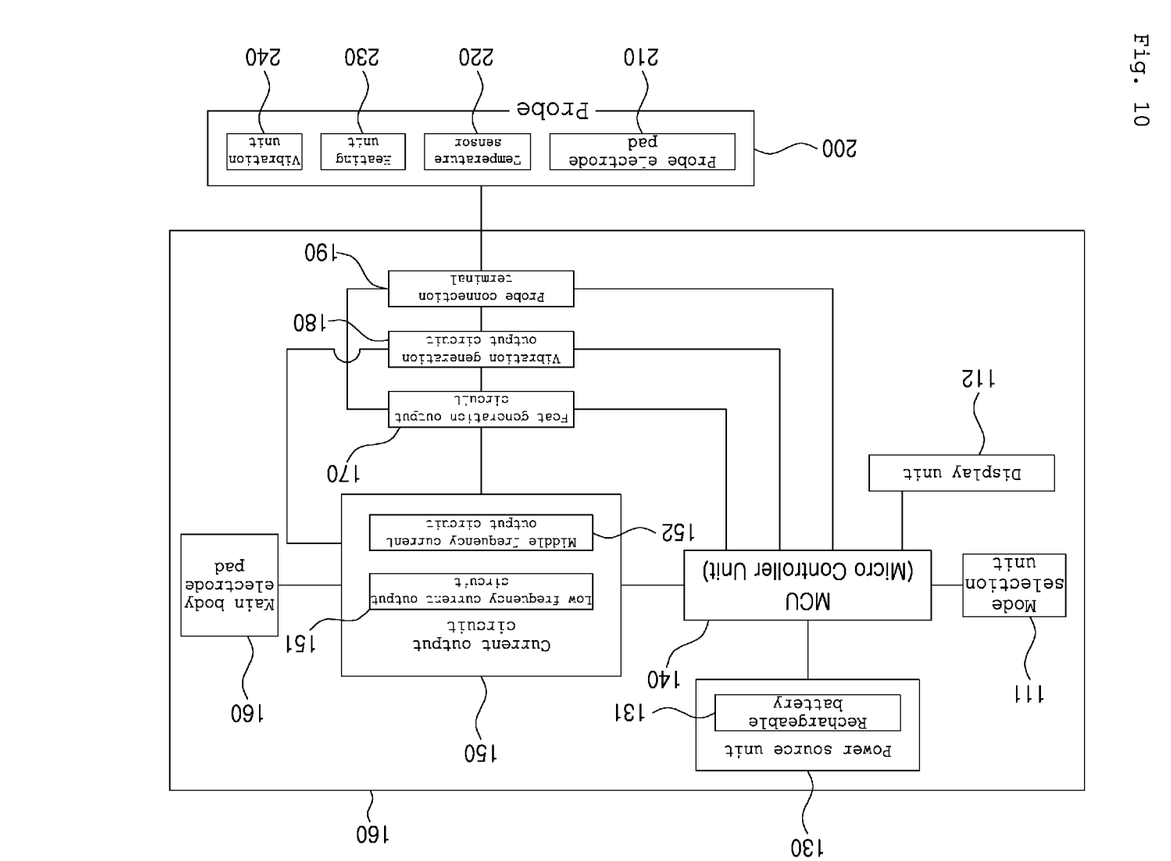

FIGS. 9 and 10 are block diagrams for illustrating the internal configuration of the portable body contact therapeutic device according to the present invention.

The portable body contact therapeutic device according to a preferred embodiment of the present invention includes a main body 100 having a first main body member 110 and a second main body member 120 coupled together in a clip form so that pants, underpants or a belt is worn in such a way as to be inserted between the facing surfaces of the first and the second main body members from one side of the main body. In the state in which pants, underpants or a belt has been inserted and worn on the main body 100, the outside surface of the first main body member 110 is formed to be directed toward the exterior of the body (specifically, the lower portion of the abdomen), and the outside surface of the second main body member 120 is formed to touch the skin of the body.

In this case, the main body 100 includes a current output circuit 150 which output an electric current. A main body electrode pad 160 through which an electric current output by the current output circuit 150 flows is formed on the outside surface of the second main body member 120.

That is, the portable body contact therapeutic device according to the present invention includes the main body 100 which has the first main body member 110 and the second main body member 120 coupled thereto, the current output circuit 150 which is included within the main body 100, and the main body electrode pad 160 which is formed on the outside surface of the second main body member 120.

The main body 100 has the first main body member 110 and the second main body member 120 coupled thereto in a clip form. That is, the main body 100 has the first main body member 110 and the second main body member 120 coupled thereto in a clip form in which pants or a belt is inserted between the facing surfaces of the first main body member 110 and the second main body member 120 from one side of the main body 100.

In this case, if pants, underpants or a belt is inserted between the first main body member 110 and the second main body member 120 and thus the main body 100 is worn on a body portion, the main body 100 is worn so that the outside surface of the first main body member 110 is directed toward the outside of the body and the second main body member 120 touches the skin of the body.

Particularly, a contact coupling member 115 of an elastic material for enabling pants, underpants or a belt to be closely attached and inserted between the inside surface of the first main body member 110 and the inside surface of the second main body member 120 is preferably further coupled to the inside surface of the first main body member 110.

That is, since the contact coupling member 115 is formed close to the inside surface of the second main body member 120, pants, underpants or a belt inserted between the first main body member 110 and the second main body member 120 can be firmly engaged and fixed to the contact coupling member 115 and the second main body member 120.

The current output circuit 150 includes a low frequency current output circuit 151 which outputs a predetermined low frequency current and a middle frequency current output circuit 152 which outputs a predetermined middle frequency current.

In this case, the low frequency current means an electric current having a frequency of 1 Hz or more to less than 1000 Hz. The middle frequency current means an electric current having a frequency of 1000 Hz or more to less than 10000 Hz.

In this case, a Micro Controller Unit (MCU) 140 to be described later controls the operations of the low frequency current output circuit 151 and the middle frequency current output circuit 152 according to setting with respect to the low frequency current and the middle frequency current suitable for a selected therapy mode.

In this case, the main body electrode pad 160, that is, a main body electrode plate, includes a low frequency electrode plate 162 through which the low frequency current output by the low frequency current output circuit 151 flows and a middle frequency electrode plate 164 through which the middle frequency current output by the middle frequency current output circuit 152 flows.

In this case, an interference wave (ICT) according to the low frequency current and the middle frequency current is generated in the main body electrode pad 160. A more effective treatment can also be performed by the generated interference wave.

That is, the portable body contact therapeutic device according to the present invention can perform very effective treatments because treatments according to the low frequency and middle frequency currents and treatments according to the interference wave are performed together.

That is, the portable body contact therapeutic device according to the present invention includes the low frequency current output circuit 151 and the middle frequency current output circuit 152 which output the low frequency current and the middle frequency current, respectively, and is configured so that the low frequency current and the middle frequency current output by the low frequency current output circuit 151 and the middle frequency current output circuit 152, respectively, flow to the main body electrode pad 160.

In this case, the main body electrode pad 160 includes the low frequency main body electrode pad 162 conductive to the low frequency current output circuit 151 and the middle frequency main body electrode pad 164 conductive to the middle frequency current output circuit 152.

The main body 100 further includes a mode selection unit 111 which includes two or more therapy modes including a urinary incontinence therapy mode and a cramps therapy mode and selects one of the therapy modes and the MCU 140 in which a proper low frequency current value and a proper middle frequency current value have been previously sets based on the therapy mode selected in the mode selection unit 111 and which controls the operations of the low frequency current output circuit and the middle frequency current output circuit so that the predetermined proper low frequency current value and proper middle frequency current value according to the therapy mode selected in the mode selection unit 111 are output.

The mode selection unit 111 is preferably installed on the outside surface of the first main body member 110.

Furthermore, a display unit 112 which displays various contents selected in the mode selection unit 111 is preferably further formed on the outside surface of the first main body member 110.

The MCU 140 is electrically connected to the mode selection unit 111 and the current output circuit 150.

A low frequency value and a middle frequency value suitable for a therapy mode selected in the mode selection unit 111 have been previously set in the MCU 140. The MCU 140 controls the operations of the low frequency current output circuit 151 and the middle frequency current output circuit 152 so that the low frequency current and the middle frequency current suitable for a therapy mode selected in the mode selection unit 111 are output to the low frequency current output circuit 151 and the middle frequency current output circuit 152, respectively.

In this case, the mode selection unit 111 may further include a user age mode selection unit which receives and selects information about the ages of two or more users.

That is, a user may input his or her age to the age mode selection unit and receive low frequency/middle frequency treatments which is suitable for his or her age group and suitable for a selected therapy mode.

In this case, a proper low frequency current value and a proper middle frequency current value according to an age selected in the age mode selection unit have been previously set in the MCU 140. The MCU 140 controls the operations of the low frequency current output circuit and the middle frequency current output circuit so that a predetermined proper low frequency current value and proper middle frequency current value according to an age selected in the age mode selection unit are output.

That is, the MCU 140 is previously programmed so that the low frequency current output circuit and the middle frequency current output circuit output the low frequency current and the middle frequency current suitable for selected age information and a selected therapy mode, respectively, based on the selection of an age mode and a therapy mode in the mode selection unit 111.

Accordingly, when a user selects his or her own therapy mode in the mode selection unit 111 and selects an age mode selection unit based on his or her age information, the MCU 140 controls the operations of the low frequency current output circuit 151 and the middle frequency current output circuit 152 so that the low frequency current and the middle frequency current suitable for the age and therapy mode of the user are output.

The main body 100 includes a probe connection terminal 190 which is connected to the current output circuit 150 so that an electric current output by the current output circuit 150 is transferred to the outside and which is connected to the main body 100 in order to enable the transmission and reception of external data.

In this case, a probe 200 is further included which is connected to the probe connection terminal 190 by an electric wire 300 and which is formed in a form inserted into a woman's vagina. A probe electrode pad 210 through which an electric current transferred through the electric wire from the probe connection terminal 190 flows is formed on the outside surface of the probe 200.

The probe 200 includes a temperature sensor 220 which measures the temperature of a surface of the probe, a heating unit 230 which generates heat, and a vibration unit 240 which generates vibration.

In this case, the main body unit 100 includes a heat generation output circuit 170 which outputs a heat generation signal so that heat of a specific temperature is generated from the heating unit 230 and which is connected to the probe connection terminal 190 so that the output heat generation signal is transmitted to the heating unit of the probe.

In this case, the MCU 140 controls the operation of the heat generation output circuit 170 so that it outputs a heat generation signal that enables a temperature sensed by the temperature sensor 220 to be maintained at a predetermined proper temperature.

That is, if a temperature measured by the temperature sensor 220 of the probe 200 exceeds a predetermined proper intravaginal temperature by a specific tolerance, the MCU 140 controls the operation of the heating unit 230 of the probe 200 by controlling the heat generation output circuit so that the predetermined proper intravaginal temperature is maintained.

Accordingly, treatments for a feeling of cold can be performed in parallel to or independently of other treatments.

When the cramps therapy mode is selected in the mode selection unit 111, the MCU 140 controls the operation of the current output circuit 150 so that an electric current does not flow to the probe connection terminal 190. When the urinary incontinence therapy mode is selected in the mode selection unit 111, the MCU 140 controls the operation of the current output circuit 150 so that only one predetermined current of the low frequency current output by the low frequency current output circuit 151 and the middle frequency current output by the middle frequency current output circuit 152 is conductive to the probe connection terminal 190.

That is, when the cramps therapy mode is selected, it corresponds to a case where treatments according to the low frequency current and/or the middle frequency current within the vagina are inappropriate. Accordingly, the MCU 140 controls the operation of the current output circuit 150 so that the low frequency and/or the middle frequency current is not output from the current output circuit 150 to the probe.

Furthermore, when the urinary incontinence therapy mode is selected, the MCU 140 performs control so that a treatment method most suitable for each therapy mode is performed by controlling the operation of the current output circuit so that treatments according to the low frequency current and the middle frequency current within the vagina are performed together.

The probe 200 further includes the vibration unit 240 generating vibration. The mode selection unit 111 includes a vibration mode selection unit in which a vibration on or off mode and one of two or more vibration intensity modes classified according to vibration intensity are selected.

In this case, the main body unit 100 includes a vibration generation output circuit 180 which outputs a vibration generation signal that enables the vibration unit 240 to generate specific vibration and which is connected to the probe connection terminal 190 so that the output vibration generation signal is transmitted to the vibration unit 240 of the probe 200.

In this case, the MCU 140 controls the vibration generation output circuit 180 so that vibration according to the selection of the vibration mode selection unit is generated from the vibration unit 240.

That is, when a user selects vibration intensity suitable for him or her, the MCU 140 controls the vibration generation output circuit 180 so that it outputs the vibration generation signal that enables vibration according to the selected vibration intensity to be generated.

Conductive adhesive pads are coupled to the main body electrode pad 160 and the probe electrode pad 210, respectively.

The conductive adhesive pads made of a material that does not stimulate or damage the body or the vaginal wall are preferably attached to the main body electrode pad 160 and the probe electrode pad 210.

Furthermore, the portable body contact therapeutic device according to the present invention further includes a UV lamp 195 capable of sterilizing the external surface of the probe 200.

In this case, a lamp button which turns on or off the operation of the UV lamp 195 may be further formed in the main body.

Particularly, the probe connection terminal 190 and the UV lamp 195 are preferably formed on the upper side of the first main body member 110. A cover 197 which opens and shuts a portion where the probe connection terminal 190 and the UV lamp 195 have been formed is preferably formed.

Furthermore, in the portable body contact therapeutic device according to the present invention, a power source unit 130 which supplies power to the current output circuit 150, the heat generation circuit 170, the vibration generation circuit 180, etc., which is connected to the probe connection terminal 190, and which supplies power to the probe 200 is included in the main body 100.

In this case, the power source unit 130 preferably includes a rechargeable battery so that it is recharged with external power.

In accordance with the present invention, such as that described above, there can be provided the portable body contact therapeutic device which can be conveniently worn on the body so that it directly touches the body and can maximize therapy effects for various woman diseases.

Those skilled in the art to which the present invention pertains will appreciate that the present invention may be implemented in other detailed forms without departing from the technical spirit or essential characteristics of the present invention. Accordingly, the aforementioned embodiments should be understood as being only illustrative, but should not be understood as being restrictive from all aspects. The scope of the present invention is defined by the following claims rather than the detailed description, and the meanings and scope of the claims and all changes or modified forms derived from their equivalents should be construed as falling within the scope of the present invention.

What is claimed is:

1. A portable body contact therapeutic device, comprising:
   a main body which has a first main body member and a second main body member coupled together in a clip form so that pants, underpants or a belt is worn in such a way as to be inserted between facing surfaces of the first and the second main body members from one side of the main body,
   wherein an outside surface of the first main body member is formed to be directed toward an outside of a body and an outside surface of the second main body member is formed to touch a skin of the body in a state in which the pants, underpants or belt has been inserted and worn on the main body, the main body comprises a current output circuit which outputs an electric current, and a main body electrode pad through which the electric current output by the current output circuit flows is formed on the outside surface of the second main body member.

2. The portable body contact therapeutic device of claim 1, wherein:

the current output circuit comprises a low frequency current output circuit which outputs a predetermined low frequency current and a middle frequency current output circuit which outputs a predetermined middle frequency current, and the main body electrode pad comprises a low frequency electrode plate and a middle frequency electrode plate through which the low frequency current output by the low frequency current output circuit and the middle frequency current output by the middle frequency current output circuit flow, respectively.

3. The portable body contact therapeutic device of claim 2, wherein the main body further comprises:

a mode selection unit which has two or more therapy modes comprising a urinary incontinence therapy mode and a cramps therapy mode and in which one of the therapy modes is selected; and a micro controller unit (MCU) in which a proper low frequency current value and a proper middle frequency current value are previously set based on a therapy mode selected in the mode selection unit and which controls operations of the low frequency current output circuit and the middle frequency current output circuit so that a predetermined proper low frequency current value and proper middle frequency current value according to the therapy mode selected in the mode selection unit are output.

4. The portable body contact therapeutic device of claim 3, wherein:

the mode selection unit further comprises a user age mode selection unit which receives and selects information about ages of two or more users, and the MCU is previously programmed so that the low frequency current output circuit and the middle frequency current output circuit output a low frequency current and a middle frequency current suitable for selected age information and a selected therapy mode, respectively, based on the age mode and the therapy mode selected in the mode selection unit.

5. The portable body contact therapeutic device of claim 3, wherein:

the main body comprises a probe connection terminal which is connected to the current output circuit so that the electric current output by the current output circuit is externally transferred and which is connected to the main body to enable a transmission and reception of external data, a probe electrode pad is connected to the probe connection terminal by an electric wire and formed in a form inserted into a woman's vagina, and the probe electrode pad through which the electric current transferred through the electric wire from the probe connection terminal flows is formed on an external surface.

6. The portable body contact therapeutic device of claim 5, wherein:

the probe comprises a temperature sensor which measures a temperature of a surface of the probe, a heating unit which generates heat, and a vibration unit which generates vibration, the main body further comprises a heat generation output circuit which outputs a heat generation signal so that the heating unit generates heat of a specific temperature and which is connected to the probe connection terminal so that the output heat generation signal is transmitted to the heating unit of the probe, and the MCU controls an operation of the heat generation output circuit so that the heat generation output circuit outputs the heat generation signal which enables a temperature sensed by the temperature sensor to be maintained at a predetermined proper temperature.

7. The portable body contact therapeutic device of claim 6, wherein:

when the cramps therapy mode is selected in the mode selection unit, the MCU controls an operation of the current output circuit so that an electric current does not flow toward the probe connection terminal, when the urinary incontinence therapy mode is selected in the mode selection unit, the MCU controls the operation of the current output circuit so that only one predetermined current of the low frequency current output by the low frequency current output circuit and the middle frequency current output by the middle frequency current output circuit flows toward the probe connection terminal.

8. The portable body contact therapeutic device of claim 5, wherein:

the probe comprises a vibration unit which generates vibration, the mode selection unit comprises a vibration mode selection unit in which a vibration on or off mode and one of two or more vibration intensity modes classified according to vibration intensity are able to be selected, the main body further comprises a vibration generation output circuit which outputs a vibration generation signal so that the vibration unit generates specific vibration and which is connected to the probe connection terminal so that the output vibration generation signal is transmitted to the vibration unit of the probe, and the MCU controls an operation of the vibration generation output circuit so that vibration selected in the vibration mode selection unit is generated from the vibration unit.

* * * * *